US011123444B2

(12) United States Patent
Macknik et al.

(10) Patent No.: US 11,123,444 B2
(45) Date of Patent: Sep. 21, 2021

(54) METHODS AND DIAGNOSTIC KIT FOR VISUALIZING BODY TISSUES AND COMPONENTS THEREIN

(71) Applicant: DIGNITY HEALTH, San Francisco, CA (US)

(72) Inventors: Stephen L. Macknik, Anthem, AZ (US); Susana Martinez-Conde, Brooklyn, NY (US); Hector Rieiro, Papillion, NE (US)

(73) Assignee: Dignity Health, San Francisco, CA (US)

( * ) Notice: Subject to any disclaimer, the term of this patent is extended or adjusted under 35 U.S.C. 154(b) by 115 days.

(21) Appl. No.: 15/031,141

(22) PCT Filed: Oct. 16, 2014

(86) PCT No.: PCT/US2014/060940
§ 371 (c)(1),
(2) Date: Apr. 21, 2016

(87) PCT Pub. No.: WO2015/061136
PCT Pub. Date: Apr. 30, 2015

(65) Prior Publication Data
US 2016/0250355 A1 Sep. 1, 2016

Related U.S. Application Data

(60) Provisional application No. 61/895,222, filed on Oct. 24, 2013.

(51) Int. Cl.
| | |
|---|---|
| *A61B 5/00* | (2006.01) |
| *A61B 8/00* | (2006.01) |
| *A61B 10/00* | (2006.01) |
| *A61K 49/00* | (2006.01) |
| *A61B 5/369* | (2021.01) |
| *A61K 9/00* | (2006.01) |
| *A61M 5/00* | (2006.01) |
| *A61B 5/026* | (2006.01) |

(52) U.S. Cl.
CPC ........ *A61K 49/0054* (2013.01); *A61B 5/0068* (2013.01); *A61B 5/0071* (2013.01); *A61B 5/369* (2021.01); *A61B 5/4094* (2013.01); *A61B 5/4839* (2013.01); *A61B 5/7282* (2013.01); *A61K 9/0019* (2013.01); *A61M 5/007* (2013.01); *A61B 5/0261* (2013.01)

(58) Field of Classification Search
None
See application file for complete search history.

(56) References Cited

U.S. PATENT DOCUMENTS

| | | | | |
|---|---|---|---|---|
| 2006/0188492 A1* | 8/2006 | Richardson | .......... | A61K 31/122 424/94.1 |
| 2009/0005711 A1* | 1/2009 | Konofagou | .......... | A61B 8/0816 601/2 |

FOREIGN PATENT DOCUMENTS

WO   WO-2012099448 A2 *  7/2012   ......... A61K 38/1709

OTHER PUBLICATIONS

Martin et al. (Cell Calcium 2006, 40, 393-402).*
Dehouck et al. (J. Cerebral Blood Flow Metab. 1997, 17, 464-469).*
Bell et al. (Neuron 2010, 68, 409-427).*
Funk et al. (Ophthalmology 2009, 116, 2393-2399).*
Appaix et al. (PLos One 2012, 74, e35169 p. 1-13).*
Guerin et al. (Neurosci. 2001, 103, 873-883).*
Caruso et al. (Anticancer Research 2009, 29, 449-454).*
International Search Report and Written Opinion dated Dec. 31, 2014 in connection with PCT/US2014/06940.
Hirase et al., "Two-photon imaging of brain pericytes in vivo using dextran-conjugated dyes," Gilia, 2004, vol. 46, Issue 1, p. 95-100.
Akerblom et al., "Heterogeneity among RIP-Tag2 insulinomas allows vascular endothelial growth factor-A independent tumor expansion as revealed by studies in Shb mutant mice: Implications for tumor angiogenesis," Molecular Oncology vol. 6 p. 333-346, 2012.
Dai et al., "Visualization and contractile activity of cochlear pericytes in the capillaries of the spiral ligament," Hearing Research vol. 254 p. 100-107, 2009.
Sarkar et al., "In vivo administration of fluorescent dextrans for the specific and sensitive localization of brain vascular pericytes and their characterization in normal and neurotoxin exposed brains," NeuroToxicology vol. 33 p. 436-443, 2012.

* cited by examiner

*Primary Examiner* — Michael G. Hartley
*Assistant Examiner* — Melissa J Perreira
(74) *Attorney, Agent, or Firm* — Quarles & Brady LLP

(57) ABSTRACT

The present disclosure is directed to methods and a diagnostic kit for producing pericyte information from a subject for identifying and/or treating a subject condition. In one aspect, a method for identifying a subject condition is provided. The method includes administering intravenously to a subject an effective amount of a solution comprising fluorescent markers to selectively label a plurality of pericytes in the subject's body. The method also includes acquiring fluorescence signals originating from labeled pericytes to produce pericyte information associated with tissues of the subject's body. The method further includes generating a report identifying a subject condition using the pericyte information. In some aspects, a treatment may be adapted using the identified subject condition.

16 Claims, 12 Drawing Sheets

METHODS AND DIAGNOSTIC KIT FOR VISUALIZING BODY TISSUES AND COMPONENTS THEREIN

CROSS-REFERENCE TO RELATED APPLICATIONS

This application represents the national stage entry of PCT International Application No. PCT/US2014/060940 filed Oct. 16, 2014, which claims the benefit of, U.S. Provisional Patent Application Ser. No. 61/895,222, filed Oct. 24, 2013, the contents of which are hereby incorporated herein by reference in their entirety for all purposes.

BACKGROUND

The present disclosure generally relates to systems and methods for identifying and/or treating a subject condition and, more particularly, to systems and methods for producing information related to a subject's body tissues and components therein.

Epilepsy is central nervous disorder in which nerve activity is disturbed by epileptic episodes or seizures that result in abnormal behavior, symptoms or sensations, as well as loss of consciousness. Damaging effects of epilepsy include sclerosis, cognitive decline, or even death. Specifically, progressive neuronal degeneration is a frequent consequence of prolonged and/or repetitive seizure activity, accumulating especially in the hippocampus. In this context, ictal, or seizure-induced, cell death has been viewed traditionally as a consequence of glutamate-induced excitotoxicity, a pathological process by which nerve cells are damaged and killed by neurotransmitters, such as glutamate, due to excessive stimulation. Excitotoxicity would enable calcium overload in a cell, thereby activating pro-apoptotic molecular cascades.

However ischemia, referring to the condition of restricted blood supply to cells in tissue, can activate the same pro-apoptotic pathways in a cell as excitotoxicity. Similarly, ischemic events due to vasodynamics in epileptic brains could therefore contribute to apoptotic ictal neuronal degeneration, and be mistaken for excitotoxicity. Some current hypotheses discount this possibility because seizure foci are hyperemic—macroscopically engorged with blood—and draining veins in the human epileptic brain are moreover hyper-oxygenated. This suggests the presence of hyperoxia rather than hypoxia within the epileptogenic focus. However, the underlying vascular mechanisms of ischemia and hypoxia observed macroscopically in regions that subsequently become epileptic foci are so far unknown. Moreover, hyperemia can theoretically contribute to the malignant effects of individual capillary vasospasms by heightening metabolic rate, thereby maximizing the oxygen deficit in neurons that simultaneously suffer from localized capillary ischemia.

Current molecular labeling technologies cannot distinguish between neural degeneration mediated by excitotoxicity and hypoxia. In addition, determining the relative contribution to cell death is further complicated by the fact that the consequences of excitotoxicity may be tested in vitro, while the impact of abnormal ictal hippocampal capillary vasodynamics can only be determined in vivo.

Considering these challenges, there continues to be a clear need of improved techniques for visualizing body tissues and components therein for purposes of identifying and/or treating medical conditions.

SUMMARY

The present disclosure overcomes drawbacks of previous technologies by providing an approach that affords a number of advantages and capabilities not contemplated by, recognized in, or possible in traditional systems or known methodologies. Specifically, the present disclosure recognizes that pericyte information, generated in vivo, may be used in identifying and/or treating a subject condition, such as a neural degeneration condition elicited by epilepsy, as well as other conditions.

Therefore, described herein are methods and a diagnostic kit or tools for producing perycite information using intravenous administration of an effective amount of a solution including fluorescent markers that can selectively label pericytes. For instance, pericytic mechanisms associated with normal and abnormal physiological functions may be identified, such as, for example, the nature or manner in which capillaries of living tissues are constricted and/or vasospasmed. Additionally, such pericyte information may be used in determining blood flow dynamics, functional correlates, as well as determining, monitoring or adapting a treatment for a subject condition.

In accordance with one aspect of the present disclosure, a method for identifying a subject condition is provided. The method includes administering intravenously to a subject an effective amount of an injectable solution comprising fluorescent markers to selectively label a plurality of pericytes in the subject's body. The method also includes acquiring fluorescence signals originating from labeled pericytes to produce pericyte information associated with tissues of the subject's body, and generating a report identifying a subject condition using the pericyte information.

In accordance with another aspect of the present disclosure, a method for treating a subject condition is provided. The method includes administering intravenously to a subject an effective amount of an injectable solution comprising fluorescent markers to selectively label a plurality of pericytes in the subject's body. The method also includes acquiring fluorescence signals originating from labeled pericytes to produce pericyte information associated with tissues of the subject's body, and identifying a subject condition using the pericyte information. The method further includes adapting a treatment using the identified subject condition.

In accordance with yet another aspect of the present disclosure, a diagnostic kit for producing pericyte information associated with tissues of a subject's body is provided. The diagnostic kit includes an injectable solution comprising fluorescent markers for selectively labeling pericytes in the subject's body, and a delivery apparatus configured for administering intravenously an effective amount of the injectable solution to a subject to selectively label a plurality of pericytes in the subject's body.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present disclosure will hereafter be described with reference to the accompanying drawings, wherein like reference numerals denote like elements.

DETAILED DESCRIPTION

Figure 1:
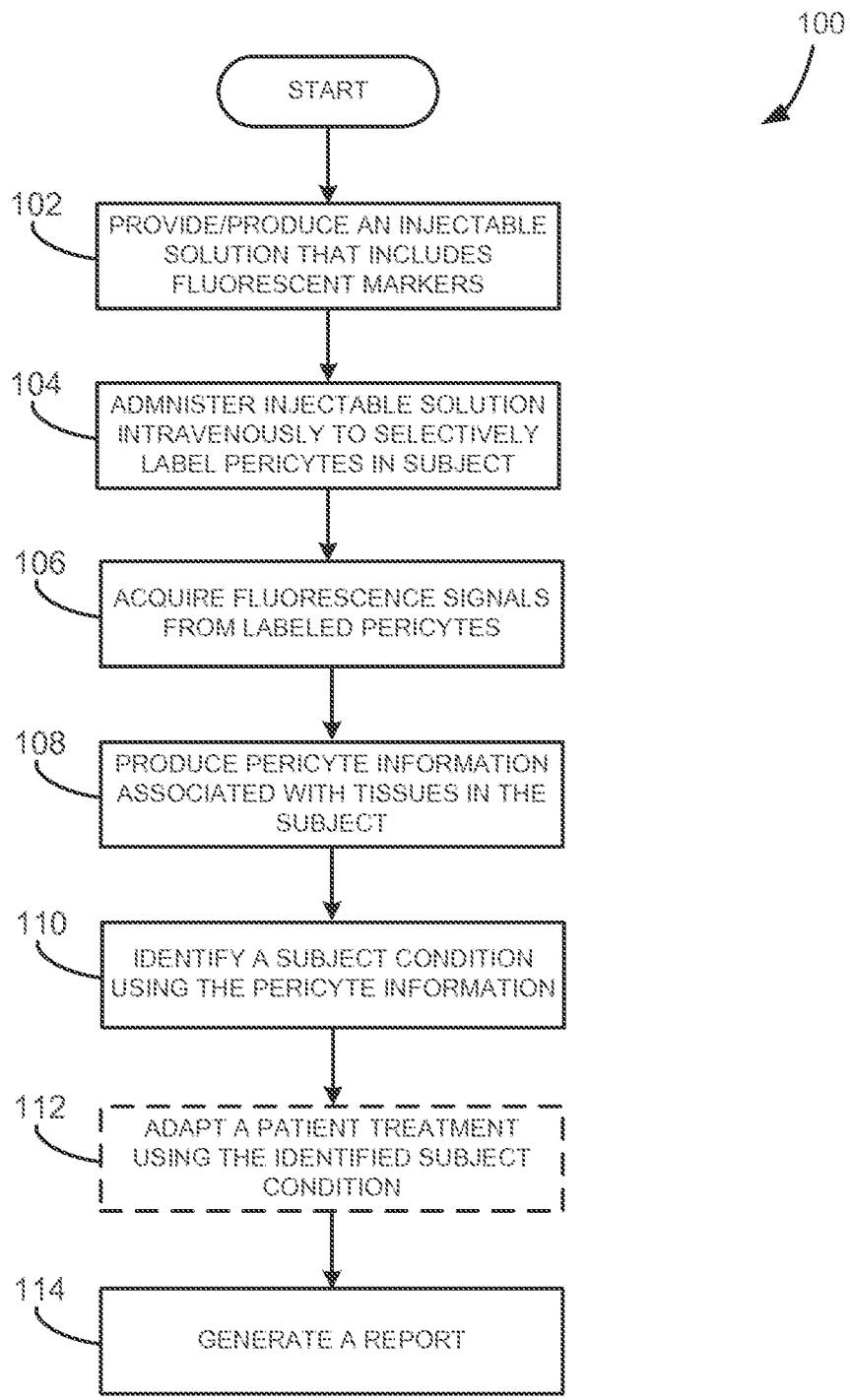
FIG. 1 is a flow chart illustrating examples of steps for a method for identifying subject conditions, in accordance with the present disclosure.

The present disclosure provides methods and systems/diagnostic kit or tools for use in generating information related to specific tissues in a subject's body, such as capillary or vascular structures, and more specifically to pericytes, which are perivascular cells that wrap around endothelial cells of capillaries and venules throughout the body, and are responsible for multiple physiological functions.

In particular, the methodology described herein is effective and efficient in non-toxically labeling pericytes in vivo via a subject's own circulatory system. This is in stark contrast to prior efforts, which attempted to label pericytes using direct focal injections of dyes. However, often such labeling procedures are not specific to pericytes, and succeed in labeling only few pericytes in locations proximate to the injection sites. Therefore, the present disclosure provides methods and a diagnostic kit directed to intravenous administration of an injectable solution including fluorescent markers that can selectively and more accurately label pericytes in a subject's body in vivo.

Advantageously, the state and/or functionality of fluorescence-labeled pericytes, in accordance with aspects of the present disclosure, can be visualized using appropriate imaging methods to identify a condition of a subject. For example, labeled pericytes may be used to determine whether certain capillary or vascular beds are functional. In addition, such pericyte information may be utilized in determining or adapting a treatment of a subject. For example, visualization of pericytes may help determine whether a vascular structure allows blood flow, and whether an intervention is necessary.

The provided methods and systems/diagnostic tools or kits may be employed as research tools to identify elements, functions, models or mechanisms associated with normal or abnormal conditions or diseases related to cardiovascular or neurovascular systems, such as constricted and/or vasospasmed capillaries caused by epilepsy. For example, a previous study has shown that activated pericytes can completely block capillary blood flow. Capillaries may further become occluded when pericytes die, and once blocked, capillary reflow may be impaired or lead to further damage. As will be explained, results using the approach of the present disclosure allow for new models related to the mechanistic pathways for neural degeneration in epilepsy to include both excitoxicity and ischemia, opening a new therapeutic pathway for abnormal blood flow dynamics in patients with epilepsy, aimed at reducing ictal cell death by reducing ischemia.

In addition, blood flow regulating drugs are currently clinically available and could thus rapidly have a major clinical benefit to reduce neural degeneration and cognitive decline for the 65 million patients with epilepsy worldwide. This would moreover be particularly important to patients with medically or surgically intractable forms of epilepsy who are especially vulnerable to ictal neural degeneration and hippocampal sclerosis such as patients with severe firms of childhood epilepsy including Lennox-Gastaut Syndrome, Dravet's Syndrome, and Phlan-McDermid Syndrome.

Referring to FIG. 1, examples of steps of a process 100 in accordance with aspects of the present disclosure are shown. Specifically, the process 100 may begin at process block 102 where an injectable solution that includes fluorescent markers is produced and/or provided. Specifically, the injectable solution includes fluorescent markers configured to at least selectively label pericytes, and produce fluorescent signals of any desired color, as will be described.

Then, at process block 104, an effective amount of injectable solution is administered preferably intravenously to selectively label at least pericytes in a subject's body. An effective amount may be configured such that a comprehensive labeling of pericytes in a subject's body is achieved. In some aspects, an effective amount of administered injectable solution may be in a dose range between 100 to 1000 microliters, for example, for small animal subjects, although it may be appreciated that dose values above or outside of this range may be desired or required to obtain sufficient or comprehensive pericyte labeling, such as for human subjects.

As described, the intravenous approach described obviates the drawbacks of current invasive approaches, whereby pericyte labeling requires dye injections directly into a desired site or tissue, resulting in few labeled pericytes randomly distributed throughout the site, as well as a diminishing number of labeled pericytes as a function of distance away from the site. By contrast, an intravenous delivery of the injectable solution, in accordance with the present disclosure, may achieve comprehensive labeling of pericytes throughout a subject's body, via the subject's circulatory system.

Fluorescence signals originating from fluorescence-labeled pericytes, and other structures in a subject's body, may then be acquired from various regions of interest, as indicated by process block 106. Specifically, fluorescent signals may be acquired using imaging systems configured for detecting fluorescent dyes in vivo. For instance, such imaging systems can utilize a confocal imaging technique and/or a two-photon microscopy technique. In some aspects, a waiting period, for example between 1 and 7 days, may be applied between process block 106 and process block 104 in order to allow for a desirable level of pericyte labeling, or desirable fluorescence signal intensities, to be reached. Additionally, other data may also be acquired from the subject, including nerve activities, blood pressure, blood oxygenation, and so forth, may be acquired and/or processed at process block 104.

Then, as indicated by process block 108, pericyte information may then be produced using the acquired fluorescence signals. In particular, pericyte information associated with specific tissues or regions of interest in a subject's body, such as capillary or vascular structures, may be produced at process block 108. For example, such pericyte information can include information related to pericyte functionality, morphology, location, size, number, separation, spatial distribution, and so on. In some aspects, pericyte information may used in combination with information obtained using other data forms or analyses, such as information from stereological analysis of immune-histochemically labeled tissues, or information related to specific physiological processes, such as nerve activities via EEG data. For instance, pericyte behavior may be correlated with seizures detected using EEG data.

Using such pericyte, and other information, as described, at process block 110 a subject condition may be identified. For example, a subject condition may include a specific vascular condition, such as the occurrence of blood flow constriction, or blood flow changes, or a neural degeneration condition. In some aspects, a likelihood of vasospasmic activity may be determined using the pericyte information.

In some aspects of the disclosure, subject conditions identified at process block 110 may be used at process block 112 to initiate, modify, or adapt a treatment. In some aspects, an identified vascular condition or a neural degeneration condition may drive a clinician to initiate the administration specific treatments or drugs, such as blood-flow regulating drugs or vasodilator drugs. Then at process block 114 a report may be generated, in any shape or form. For example, the report may include pericyte information displayed using 2D or 3D images or models. In some aspects, acquired fluorescence signals may be provided as feedback to a delivery apparatus or to a clinician in order to provide information in relation to an administered injectable solution. In other aspects, the report may include information identifying a subject condition.

In another aspect of the present disclosure, methods of the present disclosure may be performed using a diagnostic kit, or apparatus, whose advantages and capabilities will be readily apparent from descriptions below. Specifically, the diagnostic kit includes an injectable solution configured for intravenous administration, the injectable solution including fluorescent markers for selectively labeling tissues, organs, structures or biological components in the subject's body, and a diluting agent. The diagnostic kit also includes a delivery system or apparatus for administering the injectable solution intravenously to the subject.

In some aspects, the injectable solution includes fluorescent markers that may be configured to selectively label pericytes by attaching to pericytes in or about various tissues of a subject's body, and thereby producing signature fluorescent signals. By way of example, fluorescent Dextran markers, or fluorescently conjugated Dextran markers, may be utilized in the injectable solution, although it may be appreciated that other molecules, substances or compounds of similar size and/or function, may readily be substituted. In some aspects, the fluorescent markers may be described by a molecular weight in a range between 3 kiloDaltons and 70 kiloDaltons, and preferably 10 kiloDaltons, although other values may also be possible. In some applications, it may be envisioned that various fluorescent marker types may be combined in the injectable solution in order to concurrently or sequentially label, in addition to pericytes, other tissues, organs, structures or biological components in the subject's body, for example, organs, nerves, blood vessels, blood, and so forth.

The injectable solution may also include a diluting agent for diluting the fluorescent markers. For example, the diluting agent can include artificial cerebrospinal fluid ("ACSF"), or a saline, or other diluting agent that is non-toxic and has similar properties. In some aspects, the fluorescent markers may be diluted in the diluting agent to a concentration with values in a range between 16 mg/Kg and 25 mg/Kg, although other concentrations are also possible. An injectable solution, with features and capabilities, as described, is then capable of efficiently and effectively delivery of fluorescent markers for comprehensively labeling pericytes in a subject's body using the subject's own circulatory system without the drawbacks presented by direct focal injections.

The delivery apparatus of the diagnostic kit may be configured for intravenous administration to a subject, in order to selectively label a plurality of pericytes in the subject's body, as described. In some aspects, feedback with respect to a delivered injectable solution may be provided to the delivery apparatus, for example using fluorescent signals acquired from specific locations in a subject's body, in order to modify, adjust, or cease delivery the injectable solution.

The methods and systems/diagnostic tool or kit provided may be further understood by way of examples. These examples are offered for illustrative purposes only, and are not intended to limit the scope of the present disclosure in any way. Indeed, various modifications of the disclosure in addition to those shown and described herein will become apparent to those skilled in the art from the foregoing description and the following examples and fall within the scope of the appended claims. For example, specific examples of molecular dyes, doses, and so on, in association with specific procedures regarding in vivo pericyte labeling are provided, although it will be appreciated that other dyes of similar molecular size, function or dose, may also be considered within the scope of the present disclosure. Moreover, although specific examples are provided regarding administration of molecular dyes, doses, and so on, by way of intravenous techniques for pericyte labeling in animal studies, it may be appreciated that the method of the present disclosure can be extended to human subjects with appropriate adjustments, such as for example changes in dose, label, timing, subject body location and so on.

EXAMPLES

The link between epilepsy and neuronal damage was first noticed almost two centuries ago. Early work suggested that ictal vasospasms led to ischemia and neurodegeneration, but these models were contradicted later by macroscopic neurosurgical observations of hyperemia—the opposite of ischemia—at the seizure focus. Investigators concluded that seizures lead to metabolic excitotoxicity, which happens to activate the same apoptotic pathways as ischemic cell death.

Subsequently, the potential role of abnormal blood flow was pursued rarely because the hyperemia indicated no ischemia leading to neural degeneration. Recent studies, however, have localized pockets of hypoxia to the focus, and hyperemia has been shown theoretically in a quantitative computational model to exacerbate, not relieve, the malignant effects of non-uniform blood flow in capillary beds.

Before the advent of the fiber-optic-bundle-coupled laser scanning confocal fluorescence imaging technology, it has not been possible to establish the contribution of ictal pericytic-capillary vasospasms—sudden vascular constrictions that reduce the flow rate—to hippocampal neural degeneration. Though pericytes have been imaged in vitro, and in vivo, and shown to constrict in response to drug applications, no previous study has imaged spontaneous cerebral capillary vasospasms in vivo in healthy animals. In fact, the contribution of capillary vasospasm-driven hypoxia versus excitotoxicity has never before been assessed in any neurodegenerative or epilepsy disease model. Fiber-optic-coupled confocal microscopy allows for direct microscopic blood flow imaging at any brain depth. Herein, KCNA1-null mice, one of only a few genetic roden models that recapitulate human epilepsy, were studied, with relevance to human temporal lobe epilepsy. Specifically, it is shown that, for the first time, in awake and spontaneously epileptic animals and their wild-type littermates, normal and abnormal ictal hippocampal and cortical vasoconstrictions in vivo, are driven by pericytes.

Materials and Methods

Figure 2:
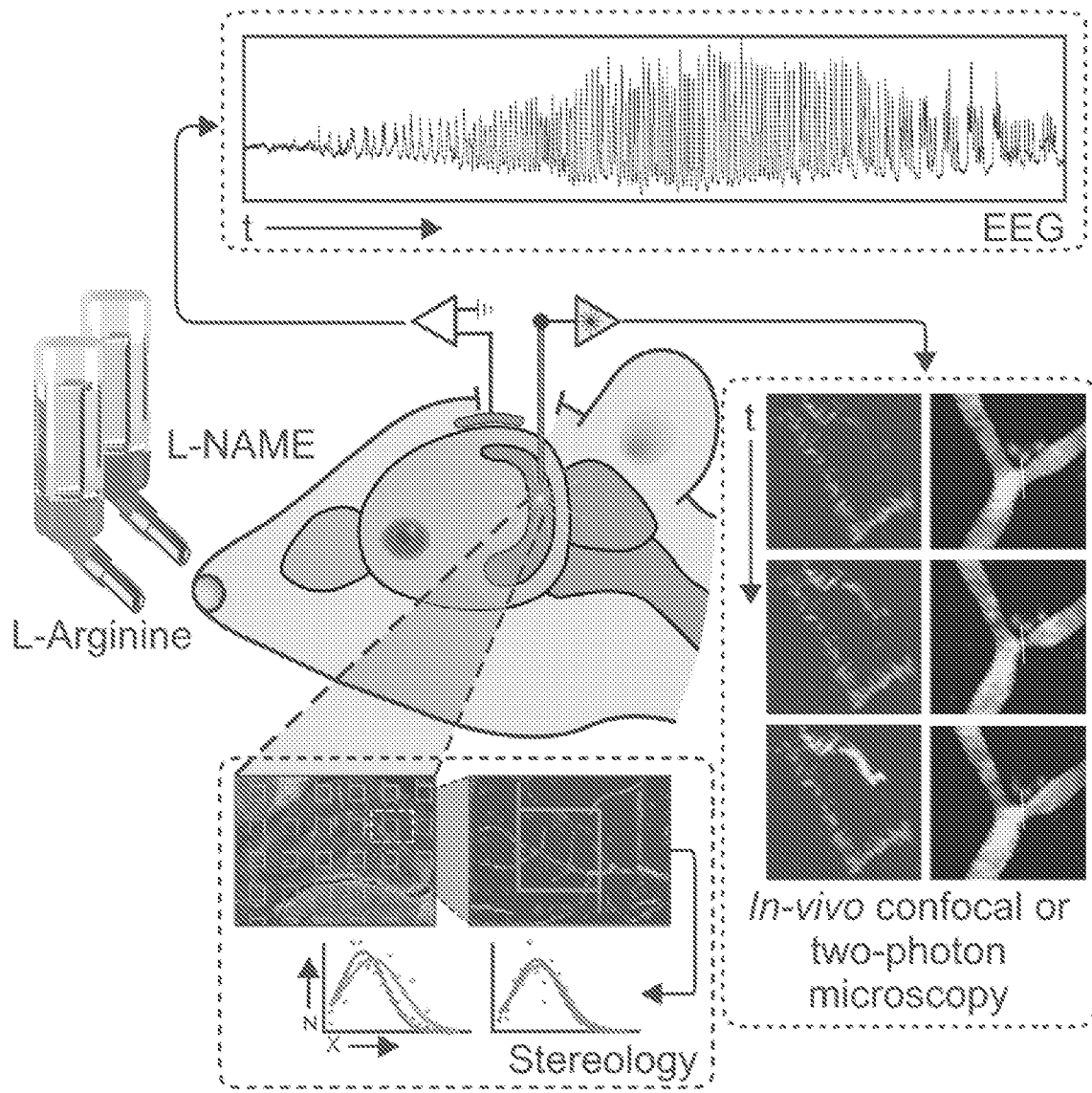
FIG. 2 is a schematic illustrating an example methodology for visualizing abnormal blood low, in accordance with the present disclosure.

Illustrated in FIG. 2 is a schematic of a methodology utilized herein. Specifically, fluorescein-coupled dextran was injected into awake Kv1.1 KO mice and their WT littermates, as well as animals created in the Kainic-acid model of epilepsy. A fiber-optic-coupled laser-scanning confocal microscope objective was positioned into the hippocampus of awake spontaneously seizing mice to visualize blood flow dynamics during EEG-determined normal, ictal, or inter-ictal periods of neural activity. To determine whether ischemia contributes to ictal neural degeneration, fixed tissue with immunofluorescent labels of cellular nuclei (DAPI) were labeled, the neuronal marker Neu-N, antibodies against α-sm-actin to visualize pericytes, and indicators of oxidative stress and apoptosis (such as antibodies against Apoptosis Inducing Factor and Caspase-3).

Figure 8:
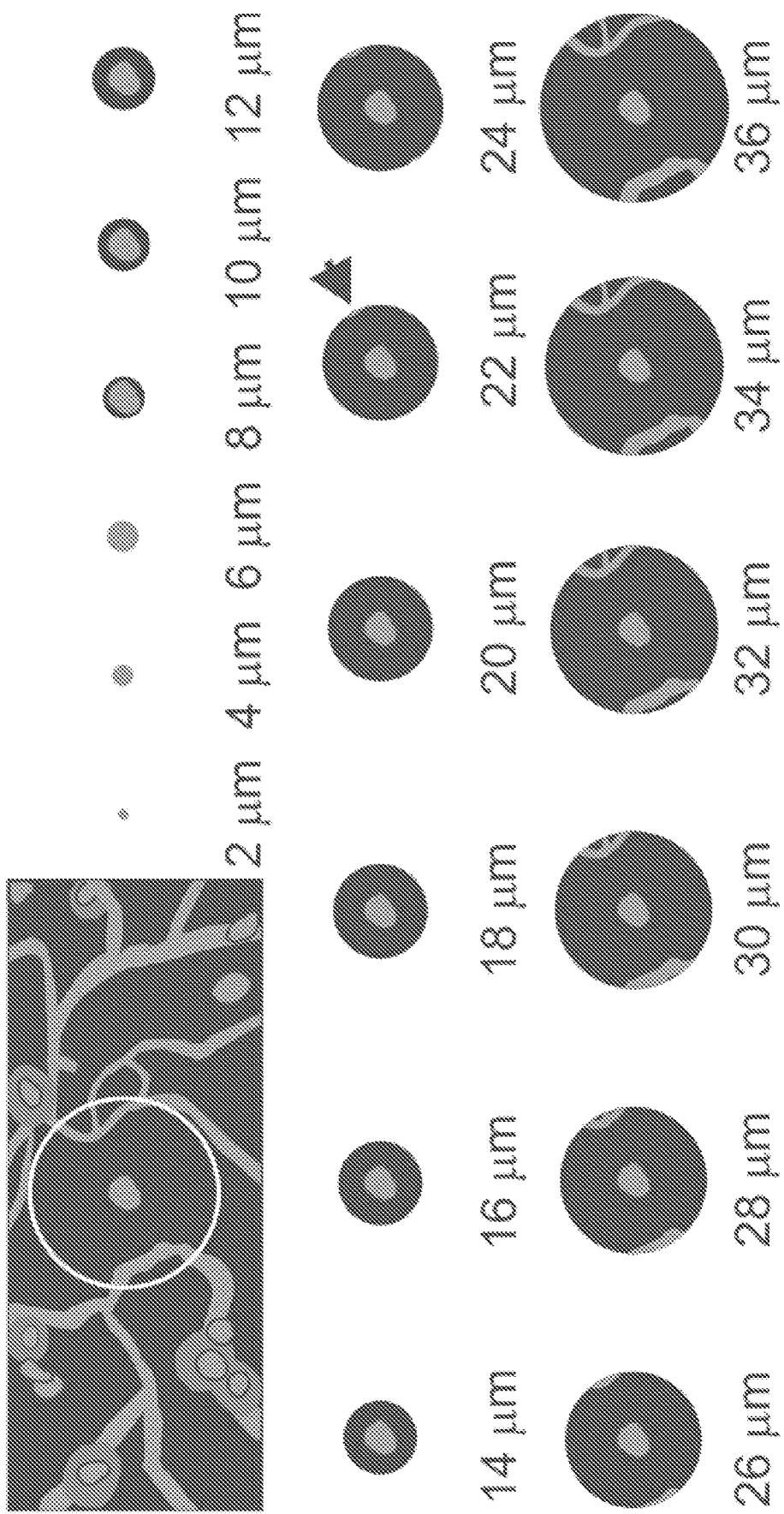
FIG. 8 is a graphical illustration of a 3D stereological method to determine cell-vessel distance, in accordance with the present disclosure.
Figure 9:
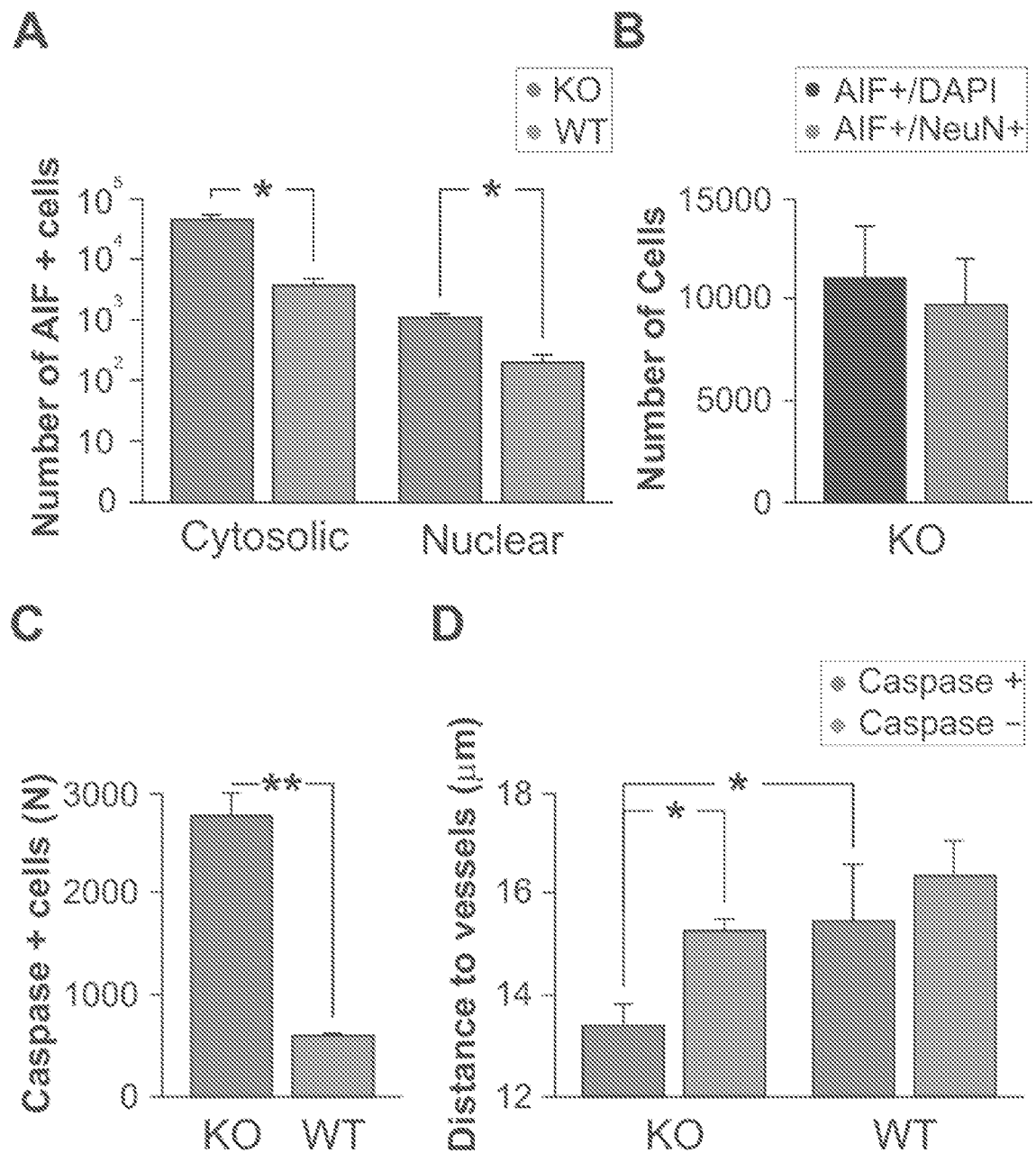
FIG. 9 is a graphical illustration of stereological analysis of dying cells, in accordance with the present disclosure.

Stereological analyses were conducted and also a 3D stereological nearest-neighbor probe was used to determine if abnormal blood flow resulted in neural damage (FIG. 8). To visualize pericytes that constricted vessels, a novel in vivo pericyte fluorescence labeling system and method was developed, which was used in a combination of dual-channel fiber-optic-coupled imaging in tree hippocampus and high spatial- and temporal-resolution TPLSM in the cortex to directly visualize pericyte constrictions during seizures and normal function. A 3D volumetric digital model of pericyte constrictions was then created from the labeled tissue. The theory that abnormal blood flow contributes to ictal neurodegeneration was tested, and the mechanistic pathway by which abnormal blood flow leads to cell death was determined by treating several cohorts of mutant and WT mice chronically with orally administered nitric-oxide based blood flow regulating drugs.

Awake Kv1.1 Animals Used in Fiber-Coupled Confocal Blood Flow Recordings

The KCNA-null Kv1.1 knockout (KO) mouse strain was obtained from the Jackson Laboratories (Bar Harbor, Me.). A total of 68 animals (34 KO and 34 wild-type (WT)) were bred in-house, and genotyped (either in-house or by Transnetyx Inc., USA) for use in these studies. Of these animals, 41 were used in the awake recording experiments, and 27 were used in the anesthetized recording experiments (see anesthetized Kv1.1 animals and fiber-coupled confocal imaging method below). All mice were maintained on a 12 h light/dark cycle. Food and water were available ad libitum. All efforts were made to minimize the discomfort and number of animals used.

The Kv1.1 KO mouse is a clinically relevant model of partial-onset epilepsy for the following reasons: 1) seizures manifest in the early postnatal period, corresponding to early childhood in humans, and are likely of limbic origin; 2) progressive histological changes in the hippocampus of these mice are similar to those observed both in human epileptic tissue and in many animal models of temporal lobe epilepsy; and 3) the KCNA1 gene—which encodes the delayed rectifier potassium channel alpha subunit Kv1.1—is one of only a few epilepsy genes in a rodent model that has a homologue in a human epileptic condition.

Pericyte Labeling

A total of 16-25 mg/kg of fluorescent Dextran, diluted in ACSF was injected intravenously (tail vein) of the animal subjects, which labeled all pericytes, as verified by double-labeling by anti-NG2 Chondroitin Sulfate Proteoglycan antibodies in subsequent histological studies (FIG. 6A-6D). In preliminary studies it was found that the molecular weight of the Dextran may be greater than 3 kD, and smaller than 70 kD, where 10 kD gave excellent results, although other values are be possible. Labeling lasted at least 6 days (the longest post-injection duration attempted), and labeling was complete roughly 16-24 hrs after injection. The labeling functioned well in adults but failed in juveniles P21 or younger for unknown reasons. Some pericytes endocytose the dye into vacuoles (as in FIG. 6P-R).

Fiber-Coupled Confocal Image Analysis

A region-of-interest (ROI) was assigned to each vessel in each movie and the changes in fluorescence as a function of time were analyzed. EEG were monitored to detect seizures continuously. Leica Microsystems (GmbH, Germany) FCM-1000 fiber-optic confocal microscope (488 nm) with 300-micron penetrating fiber-optic probes was used to precisely position surgically in the hippocampus of each mouse with a Stereodrive 3-axis robotic stereotaxic (Neurostar GmbH, Germany). On-board image analysis software was used to create ROIs of each recorded vessel. From these, an independent measure of each vessel's fluorescence-over-time ($\Delta F/F$) was derived (shown in FIG. 4A).

Using fluorescence measures, the rate of vasospasms, the percentage of time that vessels vasospasmed, individual vasospasm duration, vasospasm magnitude, and onset and termination speeds were calculated (shown in FIG. 4B-G) The experimenter who collected the data was not blind because only the KO mice have spontaneous seizures, thus she could identify KO or WT by animal's behavior or EEG. Experimenter bias was controlled, however, by keeping the image analyst blind to the cohort. In addition, this blind analyst measured vasospasm internal dynamics automatically and objectively via custom MATLAB (Mathworks, Natick, Mass.) software. Metrics across animals were averaged in each cohort and tested the significance of the difference between cohorts with standard two-tailed unpaired Student's t-tests.

The seizure rate was assessed as a function of vasospasm onsets, separately for each KO mouse (n=21). The pooled chance probability of seizure onset, the baseline seizure rate, was determined by shuffling the seizure onset times with 10,000 random permutations, and assigning the resultant correlation to vasospasms as baseline (0% level) in the analysis. Then the actual seizure times were correlated to vasospasms to create a histogram of normalized seizure onset rates as a function of vasospasm onset time. To visualize directly fluorescently labeled pericytes during hippocampal blood flow recordings, a new Dual-Band Cellvizio fiber-optic-coupled confocal microscope Mauna Kea Technologies (Paris, France), was used, where labeled pericytes was achieved using the novel method of the present disclosure and recordings were conducted in WT mice (N=4) that were either treated or untreated with KA (or both, by recoding before and after KA treatments).

Two-Photon Laser Scanning Microscopy and Analysis

WT mice (N=12) were imaged in the parietal cortex with a custom Prairie Technologies (Madison, Wis.) Ultima IV in vivo two-photon microscope powered by a Spectraphysics DeepSee Mai Tai HP (Mountainview, Calif.) Titanium: Sapphire laser. The microscope was developed with an integrated intrinsic signal optical recording setup (Optical Imaging Inc.), using epi-illumination powered by a Till Photonics (GmbH, Germany) Polychrome 5000 monochromator. Image analysis followed the analysis described for fiber-optic confocal recordings and was carried out with ImageJ.

Oral Admiration of Blood-Flow Regulating Drugs

Oral vasoconstrictors and vasodilators were administered to WT and KO mice, by diluting L-NAME (0.5 mg/ml; Sigma) or L-Arginine (1.25 g/L; Sigma) in their drinking water, starting at age P21, for a duration of 3 weeks. The animals were then sacrificed, and their brains fixed in paraformaldehyde 4% for 24 h, and cryoprotected for 24 h in 20% sucrose and for another 24 h in 30% sucrose. Finally, the brains were cut in 50 micrometer sections for further immunohistochemical and stereological analyses.

Statistical Analysis of the Sources of Neurodegeneration

To quantify the effect of the drug treatments on cell death, an analysis of covariance was performed where the probability of any given AlF+ cell across the different treatments (and the sham controls) in KO animals was compared as a function of distance between cells and vessels (2814 cells in the untreated group, 2913 cells in the L-ARG group, and 4001 in the L-NAME group). Since the L-Arginine treated animals suffer from cell death caused by excitotoxicity, while the effects of vasoconstrictions are greatly reduced, they were used as a baseline to estimate the effects of blood flow related cell death. The estimated probability of a cell being AlF+ due to excitoxicity was only therefore 25.6%. Using contrasts, it was found that the sham KO animals suffer from an increase in probability of 17.3±1.2%, while animals treated with LNAME experience a decrease of 6.8±1.1%. These differences are statistically significant (Tukey HSD, $p<0.001$). These numbers translate to an increase of 66.1% in the total number of AlF+ cells in the sham animals when compared to the L-Arginine treatment group, while the L-NAME treated animals have a 26.7% decrease. Further, the results for the WT show a non-significant increase in cell death (2.1+/−1.0%, Tukey HSD, p_0.17, 3099 cells in the untreated group, 3942 cells in the L-ARG group). Moreover, a small significant increase was found for the L-NAME group (3.8+−0.9%, Tukey HSD, $p<0.001$, 3942 cells in the L-ARG group, 3626 cells in the L-NAME group).

Results

Figure 3:
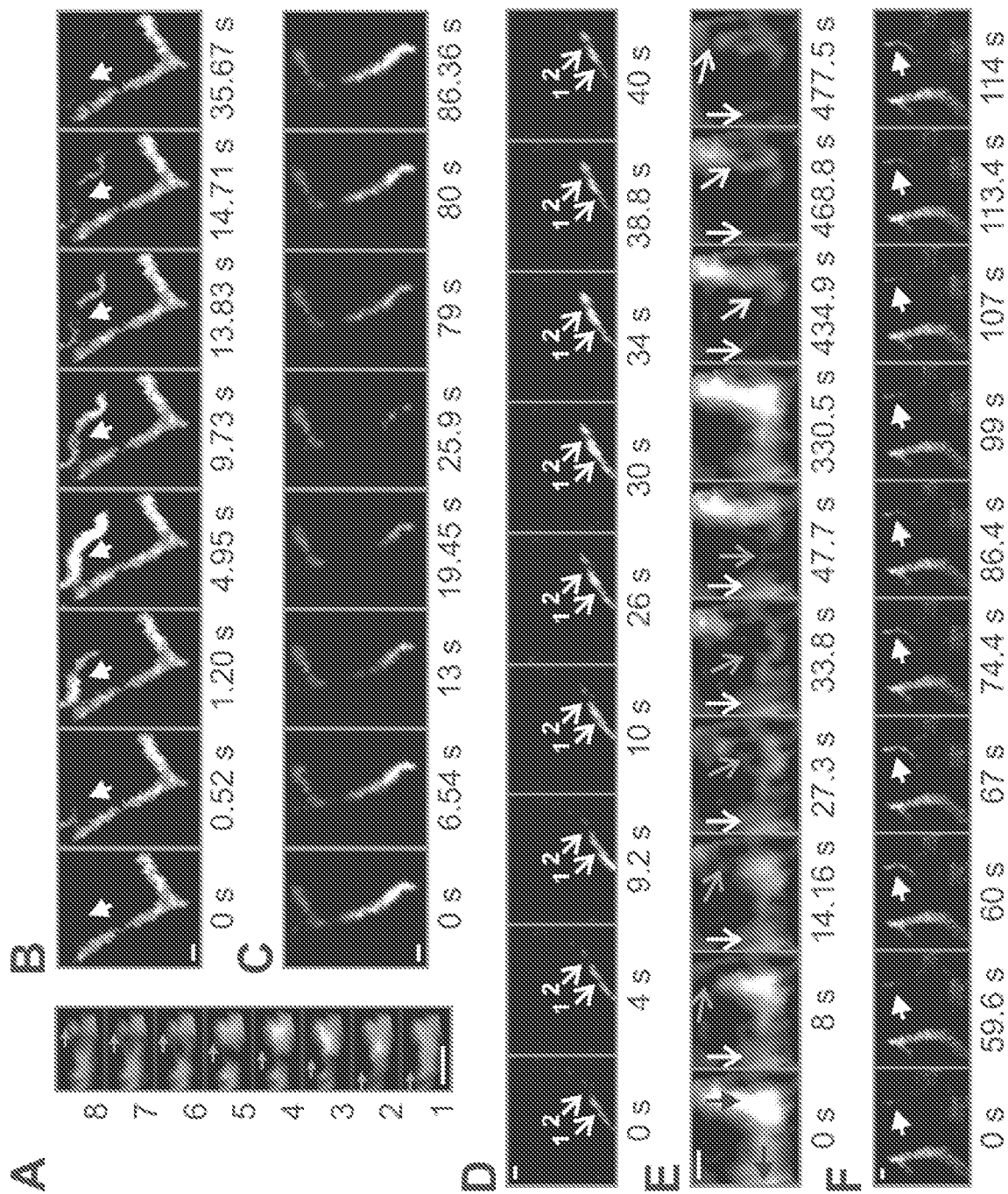
FIG. 3(A)-(F) are fiber-coupled laser-scanning confocal images of hippocampal capillaries, in accordance with the present disclosure.
Figure 4:
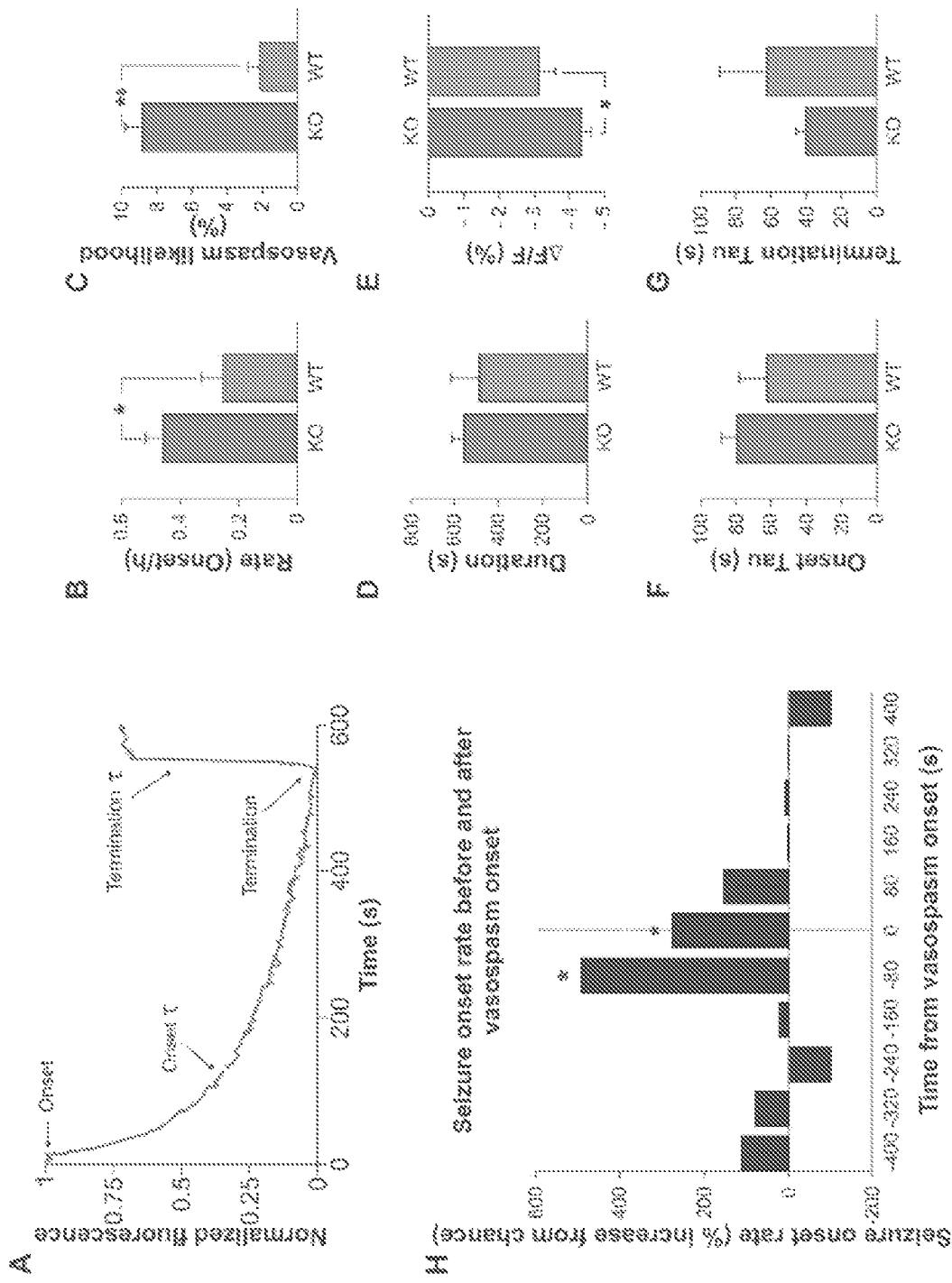
FIG. 4(A)-(H) are graphical examples illustrating vasodynamics in awake Kv1.1 KO mice versus WT littermates, in accordance with the present disclosure.

Fiber-Coupled Laser-Scanning Confocal Imaging of Hippocampal Capillaries In Vivo A total of 1154 vessels were recorded with a fiber-optic coupled laser-scanning confocal microscope from Kv1.1 KO mice and their WT littermates (703 vessels in KO mice, and 451 in WT littermates): 9% exhibited pericyte-driven vasospasms in KOs as opposed to 2% in WTs (as illustrated in FIG. 3). The average rate of vasospasms was higher in KOs (t(1004)=2.11; p=0.035, labeled *), as was the likelihood of vasospasms per vessel, expressed as a percentage of the total recording time per vessel (t(1100)=6.05; $p<1\times10-8$, labeled *8), and the average vasospasm magnitude (t(81) =2.00; p=0.049, labeled *). There was no difference between cohorts for the average vasospasm duration (t(55)=0.52; p=0.61), or the average vasospasm onset (t(52)=0.93; p=0.36) and termination speeds (t(36)=−0.84; p=0.40) (FIG. 4). The classical awake kainicacid mouse model of epilepsy rendered the same results, suggesting that the effects observed are not specific to the Kv1.1 mutation, but generalize to other forms of epilepsy.

Pericytes contain the same KCNA1 potassium channel found neuronally, which is knocked out in Kv1.1 mice, so tests were conducted as to whether seizure-independent vasospasm events caused the abnormal blood flow, by examining the potential causal relationship between seizures and vasospasms (FIG. 4H). The bin at −80 secs was significantly greater than chance at p=0.0002; at 0 sec, p=0.004 (determined by random permutation statistics). No other time points in the window from −400 secs to 400 secs reached significance. This suggests that microscopic vasospasms tend to occur within 80 seconds after seizure onset. It follows that, whereas seizures may trigger capillary vasospasms, it is less common that capillary vasospasms trigger seizures. These findings do not preclude the possibility that hypoxia occurs macroscopically before the seizure, however, perhaps due to the initial depletion of oxygen due to metabolic demands of the tissue (rather than vasospasms) around the time of the incipient seizure.

Vasospasms in WT animals were recorded as well, though they occurred less frequently than in epileptic KO littermates (FIG. 3F; FIG. 4B,C). These are the first spontaneously occurring vasospasms seen in vivo, and their occurrence in normal animals supports the growing literature suggesting that in vivo capillary vasospasms contribute to normal blood flow control within capillary beds. Clearly, blood flow in capillary beds is not controlled completely by pre-capillary sphincters on arterioles.

Figure 5:
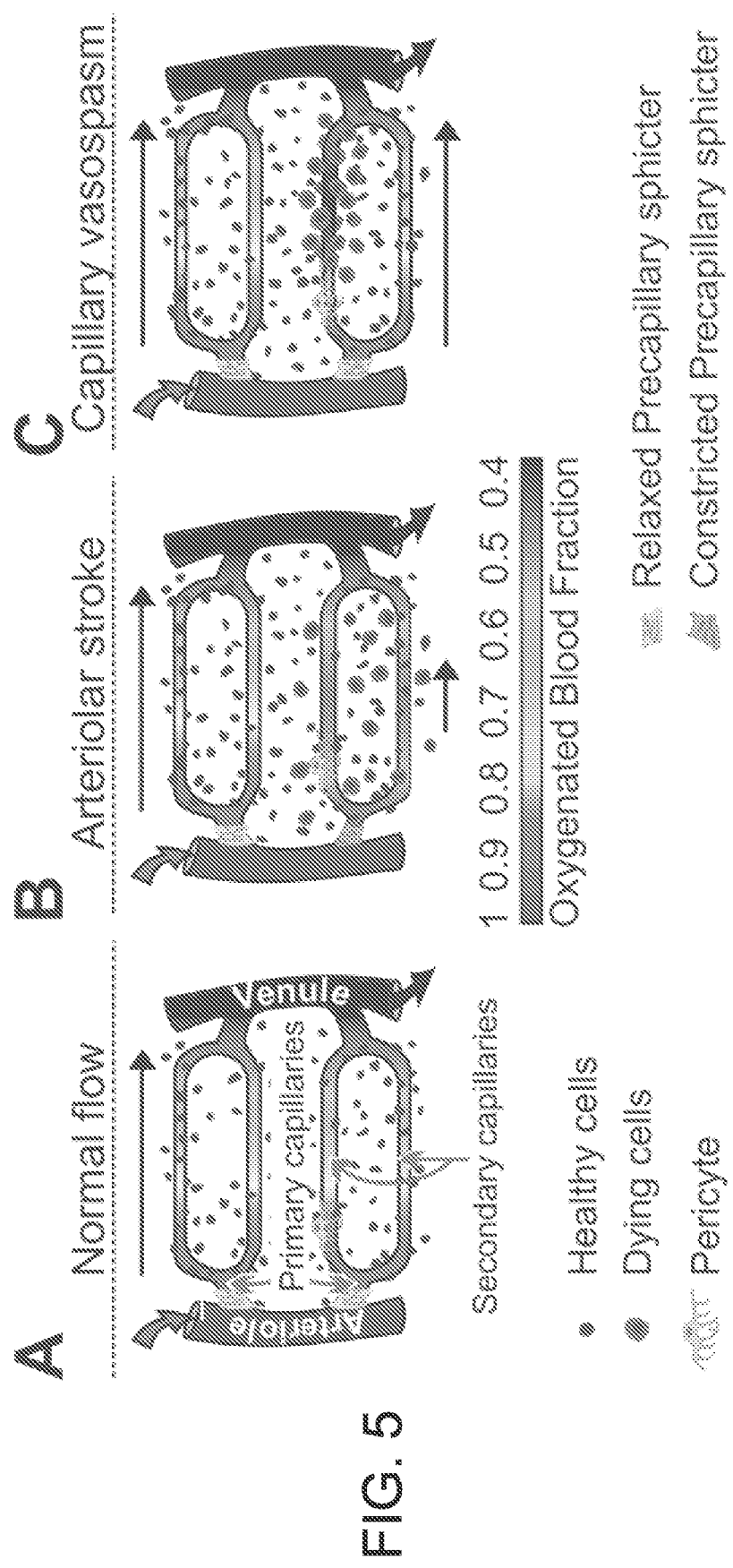
FIG. 5(A)-(C) are schematics representing models of blood flow control, in accordance with the present disclosure.

The conventional notion in tissue oxygenation suggests that perfusion is lowest between vessels, the "watershed areas" (FIG. 5A), where neurons are particularly vulnerable to ischemia during stroke (FIG. 5B). Watershed areas between two or more obstructed arteries are the most vulnerable areas after a major stroke because they are the regions farthest from the blood supply. Our logic flows from the same general idea, though now at the microscopic level. It was found herein that individual ictal vasospasms occur in isolated capillaries. That is, only 2% of capillaries undergo vasospasm at any given time in WT animals—this value rises to 9% in KO animals (FIG. 4C). It follows that, during a capillary vasospasm, the neurons farthest from the oxygen supply are the ones nearest to the blocked/constricted vessel, FIG. 5C).

It follows further that microscopic inter-capillary watershed areas are the regions of lowest vulnerability during seizures, because they have the best and most redundant oxygen perfusion, providing a measure of protection from occlusion in individual nearby vessels. Therefore, if capillary vasospasms contribute to ictal ischemic-hypoxic neuronal oxidative stress, degeneration, and death, the affected neuronal population should be spatially associated with the vasculature. The corollary to this is that, if excitotoxicity is instead the sole contributor to apoptosis, then degenerating cells—measured with immunohistochemistry for Apoptosis Inducing Factor (AIF+) and Caspase-3—will not be associated to the vasculature, because excitoxicity is not associated with the blood supply (FIG. 5B).

Analysis of Pericytes in Microvessel Strictures

To investigate the mechanistic basis for capillary constrictions or vasospasms, a new selective pericyte labeling technique was developed, which that could be used in vivo, anywhere in the body and in any color, and used in conjunction with fluorescence microscopy. A transgenic mouse with a fluorescent protein tagged to NG2 could have potentially been used, but by developing a new injectable label facilitated use it in any wild-type animals, or in mutant and/or chemically treated animals with epilepsy. A label was developed using 10 kD fluorescently-conjugated Dextran. A working hypothesis, verified herein, was that the direct brain injections functioned by vascular uptake and transport of the dye for later deposit in distant pericytes. A set of 200 µL intravenous tail vein injections were used to obtain comprehensive labeling of capillary pericytes throughout the body.

It was shown that the fluorescent dextran labeling technique is selective for pericytes by double-labeling pericytes immunohistochemically with antibodies against the pericyte biomarker NG2, (FIG. 6A-D). A dual-band Cellvizio fiber-optic-coupled confocal microscope (Mauna Kea Technologies, Paris, France) was then used to simultaneously image hippocampal vessels (with injected 2MD fluorescein Dextran) and pericytes (labeled through IV injection of 10 kD AlexaFluor 647 1-6 days previous) in C57BJ mice (3 mice were imaged without/before injection of KA, and 3 mice were imaged after subcutaneous KA injection and onset of status epilepticus), (FIG. 6E-H). Non-uniform capillary flow patterns and vasospasms (27 flow stoppages in a total of 42 capillary microvessels imaged) were observed in both untreated mice and during seizures, as in our previous experiments (FIGS. 3,4). However it was confirmed that pericytes were colocalized to the flow changes through direct fluorescent labeling of the pericytes.

To obtain high-resolution imaging of pericytes producing nonuniform flow patterns in capillary beds, two-photon laser scanning microscopy (TPLSM) was utilized in parietal cortex of WT C57BJ mice that were IV injected 1-6 days previously with 10 kD Dextran conjugated to Alexa Fluor 647 to label pericytes, and which were also injected IV immediately previous to the recording with 2MD fluorescein Dextran to image blood flow (N=12) (FIG. 6l). The animals were first imaged untreated, and then were subcutaneously injected with KA to induce status epilepticus. A total of 635 capillary microvessels were imaged with TPLSM, including 35 constrictions/vasospasms (5.5%). this number is lower than that observed in the hippocampal experiments (FIGS. 3,4), and this may reflect the fact that ictal neurodegeneration is a clinical focus in hippocampal sclerosis, not in the cortex.

Figure 6:
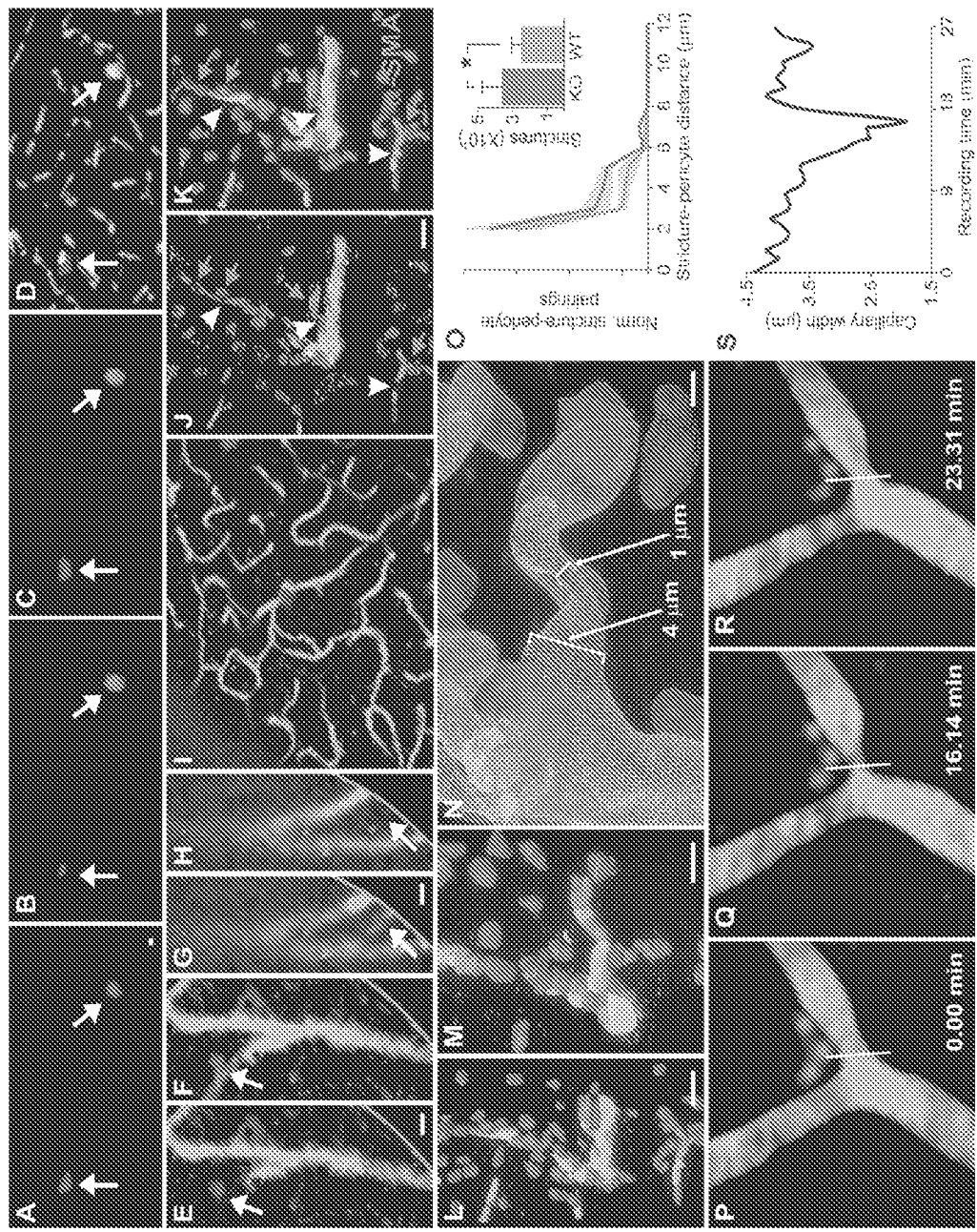
FIG. 6(A)-(S) are graphical illustrations representing analysis of pericyte vasoconstrictions, in accordance with the present disclosure.
Figure 7:
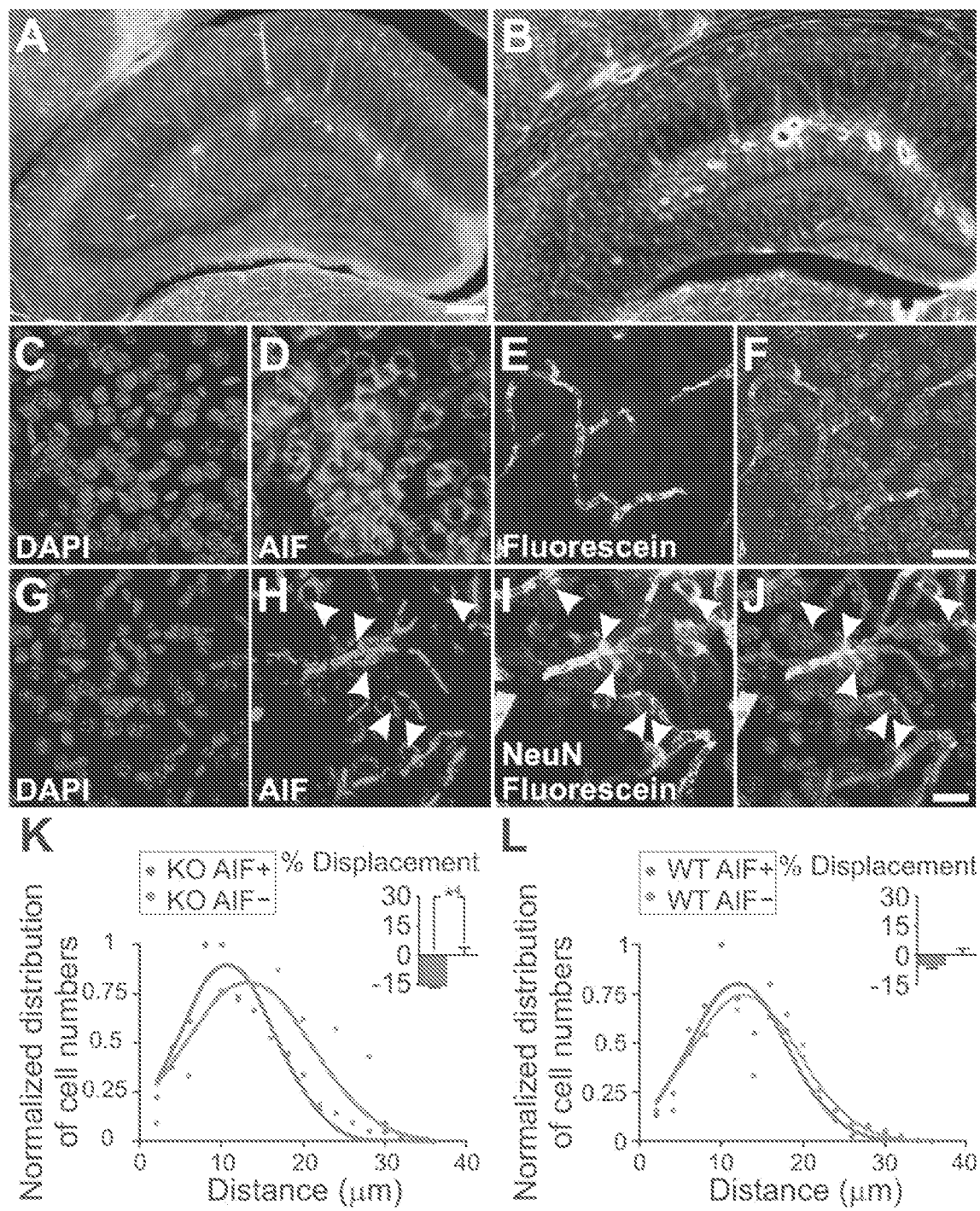
FIG. 7(A)-(L) are graphical illustrations representing the contribution of abnormal capillary vasodynamics to neural degeneration in KO and WT mice, in accordance with the present disclosure.

To quantify the role of pericytes in producing microvessel strictures in epilepsy, tissues were prepared for subsequent traditional confocal and stereological analysis in KO mice (N=3) IV injected with 2MD fluorescein Dextran to label vessels in green, then sacrificed the animals, processed the hippocampal tissue histologically and sliced it into 50 µm sections, labeled cellular nuclei in blue with the DNA-binding dye, 4',6-diamidino-2-phenylindole dihydrochloride (DAPI), and immune-histochemically-labeled pericytes in red with anti-α-smooth muscleactin primary antibodies (α-SMA) with Cy3 secondary antibodies, (FIG. 6). FIG. 6K-N shows 3D volumetric modeling of a typical microvessel stricture (vessel is constricted to 1 µm, down from its 4 µm unconstricted diameter), which blocked proximal blood flow completely in this vessel, and which is completely surrounded by a pericyte.

To quantify the role of pericytes in microvessel strictures in epilepsy, a stereological analysis of KO vs. WT microvessel strictures was conducting, with results showing that KO mice exhibit significantly more (59%) hippocampal microvessel strictures than WT mice (p=0.0418, 2-tailed Wilcoxon signed rank test), see FIG. 6O (inset). Further, stereological distance analysis reveals that most strictures in both KO & WT cohorts are within 2 µm of a pericyte (FIG. 6O). FIG. 6P-S quantifies a pericyte constriction that was imaged with high-magnification TPLSM, revealing that pericyte constrictions have slow onset dynamics and fast termination dynamics, conforming the dynamics seen in hippocampal vasospasms with fiber-optic-coupled imaging (FIG. 4F,G).

Spatial Association Between Hippocampal Neurodegeneration and Microvessels

To quantify the contribution of abnormal capillary vasodynamics to neural degeneration in KO and WT mice, sections of hippocampus were prepared for histological analysis, following each fiber-optic-coupled confocal recording. The sections were stained with DAPI, to highlight cell nuclei in blue, and with AIF primary antibodies tagged with red fluorescent Cy3 secondary antibodies, to identify cells that have engaged apoptotic pathways (FIG. 7A-J). Vessels were already stained green with 2MD fluorescein dextran during the fiber coupled confocal recordings.

Stereological methods were applied to randomly sample and count neurons, and a novel technique was developed to measure the 30 distance between each individual hippocampal AIF+ or AIF− cell and its nearest blood vessel. As illustrated in the example of FIG. 8, a starting point was centered three-dimensionally at a selected DAPI+ nucleus. A sphere was sequentially increased in 2 µm radius steps, until a flurescein-stained vessel was unmasked. The distance of the nearest blood vessel to the central DAPI+ nucleus was determined as the radius of the smallest sphere that containing a vessel. In the example of FIG. 8, a vessel was visible at a radius of 22 µm. Cell counts were then binned by distance as a function of both cohort (KO vs WT) and whether they were AIF+/−. These cell counts created the distance measurements in FIGS. 6, 7, 9 and 10A-10D.

It was found that AIF+ cells were more numerous in KO mice than in WT mice (FIG. 4A,B). Also, AIF+ cells were, on average, 15.17% (+/−0.07% s.e.m.) nearer to blood vessels than AIF− cells ($\chi2(1, N=1146)=16.70$, p<0.0001) in KO mice, whereas there was no difference ($\chi2(1, N=743)=1.976$, p=0.1598) in WT littermates (FIG. 7K,L). AIF− cells were also not significantly farther from vessels in KO mice than in WT mice ($\chi2(1, N=388)=1.287$, p=0.2566), suggesting that non-degenerating cells in KO mice are normal. AIF+ cells near capillaries in KO mice were significantly closer to vessels than AIF+ cells in WT animals ($\chi2(1, N=1541)=5.907$, p=0.0151), supporting the idea that cells undergoing apoptosis in KO mice are more likely to be doing so due to vascular effects.

To ensure that the oxidative stress measured with AIF was occurring in neuronal cells, interleaved sections of the same tissue were stained with primary antibodies to the neuron-specific biomarker (n=3 KO animals), Neu-N (FIG. 7I,J). It was found that an average of 87% (+1/−23%) of the AIF+ cells were Neu-N+ neurons (FIG. 9B). The AIF+/Neu-N+ count was not significantly different to the AIF+/DAPI+ cell count, however, the possibility that all AIF+ cells were neurons cannot be ruled out.

Although cytosolic AIF positivity indicates oxidative stress in neurons and serves as an excellent indicator of the spatial association between oxidative stress in cells and vessels, it was determined that a subset of AIF+ cells escalate from oxidative stress to death in two ways. First, while cytosolic AIF labeling is known to indicate oxidative stress, nuclear-translocated AIF labeling indicates cells actively committed to apoptotic ischemic-cell death. Therefore AIF cytosolic was counted versus nuclear labeling (FIG. 9A), as compared to AIF− cells (in both KO and WT cohorts), and a significant number of neurons was found with both cytosolic and nuclear AIF labeling (two-way ANOVA $F(1,14)=9.70$; $p=0.0076$). These AIF+ cell counts also revealed that WT have fewer dying cells than KO mice ($F(1, 14)=7.70$; $p=0.0149$), and that there was a significant interaction between AIF-labeling and cohort ($F(1, 14)=7.07$; $p=0.0187$) in which KO mice showed a significant difference between cytosolic and nuclear AIF staining (two-tailed $t(3)=4.330$; $p<0.01$ (Bonferroni corrected)), but WT animals did not. This indicates significantly more oxidative stress leading to neuronal death in KO animals than in WT animals.

It was further confirmed that the AIF+ population of neurons was dying by probing interleaved sections of the tissue with primary antibodies against active caspase-3, which is part of an AIF independent pro-apoptotic molecular cascade, important to both ischemic cell death and excitotoxicity. Using stereological analyses, it was found that caspase+ cells were more prevalent in KO mice than in WT mice (two-tailed $t(4)=5.979$; $p=0.0039$), and that caspase+ cells were spatially associated (significantly nearer) to vessels in KO mice (two-tailed Mann-Whitney $U=52805$; $p=0.0040$), but not in WT mice (FIG. 9C-D). Further, seizures resulted in tighter association of AIF+ cells to vessels in the epileptic WT mice treated with kainic acid ($\times 2(1, N=1422)=34.32$, $p<0.0001$).

Blood-Flow Regulating Drug Treatment Effects on Neurodegeneration in Epilepsy

Nitric oxide (NO) is involved in regulating blood flow through vasodilatation and hypotension. By treating a new group of Kv1.1 KO mice and their WT littermates with a nitric oxide synthase inhibiting drug—L-NAME—the mechanistic basis by which abnormal blood flow leads to cell death was determined. An early hypothesis was that vasospasms led to hypoxia through a simple process of ischemia—decreased blood flow leads to decreased oxygen which in turn leads to increased vascularly-associated oxidative stress and death. For example, when healthy WT animals are treated with L-NAME, their AIF+ cells (FIG. 10A, red) become more tightly associated to the vasculature as compared to their untreated counterparts (FIG. 10A, black), ($\times 2(1, N=1492)=13.72$, $p<0.0002$). But a recent novel computational model of capillary blood flow showed that hyperemia can exacerbate cell death in the face of heterogeneous capillary blood flow restrictions. The logic applies here that hyperemia in the ictal focus leads to high metabolic rate, and neurons spatially associated with the individually vasospasming vessels will thus suffer from an even greater oxygen deficit than they might if they had a lower metabolic demand (under nonhyperemic conditions).

It follows that if L-NAME administration tightens the association between neurodegeneration and the vasculature in KO mice as well, it would indicate that the simple hypoxia hypothesis was correct in epilepsy: blood flow suppression maximizes ischemia and leads to deeper hypoxia. But if L-NAME instead dissociates vessels from dead/dying cells in KO mice, and if oxidative stress is greatly reduced by L-NAME blood flow suppression—with lower metabolic demands being neuroprotective in the presence of vasospasms—it would indicate that hyperemia contributes to the malignant effects of the vasospasms, and that the precise mechanistic pathway of neurodegeneration driven by abnormal blood flow is the combination of hyperemia and non-uniform blood flow in capillary beds. This latter model was verified with a significant reduction in oxidative stress and vascular spatial dissociation in L-NAME treated AIF+ neurons in KO animals, as compared to AIF+ neurons in untreated KO animals (FIG. 10C, red), ($\times 2(1, N=1952)=11.67$, $p<0.0006$). This finding was further verified by a significant increase in survival—and vascular spatial dissociation of AIF− neurons—in L-NAME treated KO animals compared to the untreated KO cohort (FIG. 10D, red), ($\times 2(1, N=4863)=56.82$, $p<0.0001$).

To determine whether vasodilatation ameliorates ictal neurodegeneration, an NO donor and blood flow enhancer-L-Arginine- was orally administered to a third cohort of Kv1.1 mice and their WT littermates, applying the same protocols and analysis used with the L-NAME and untreated cohorts. The vasodilator significantly decreased oxidative stress and increased the number of healthy cells in KO mice leading to a reduction in oxidative stress and vascular spatial dissociation of L-Arginine treated AIF+ neurons in KO animals as compared to AIF+ neurons in untreated KO animals (FIG. 10C, blue), ($\times 2$ $(1, N=2154)=86.01$, $p<0.0001$), with a significant increase in survival and vascular spatial dissociation of AIF− neurons in the O LArginine treated versus untreated cohorts (FIG. 1 OD, blue), ($\times 2$ $(1, N=4293)=134.2$, $p<0.0001$). A schematic representation of this model is shown in FIG. 11A-C.

Figure 10:
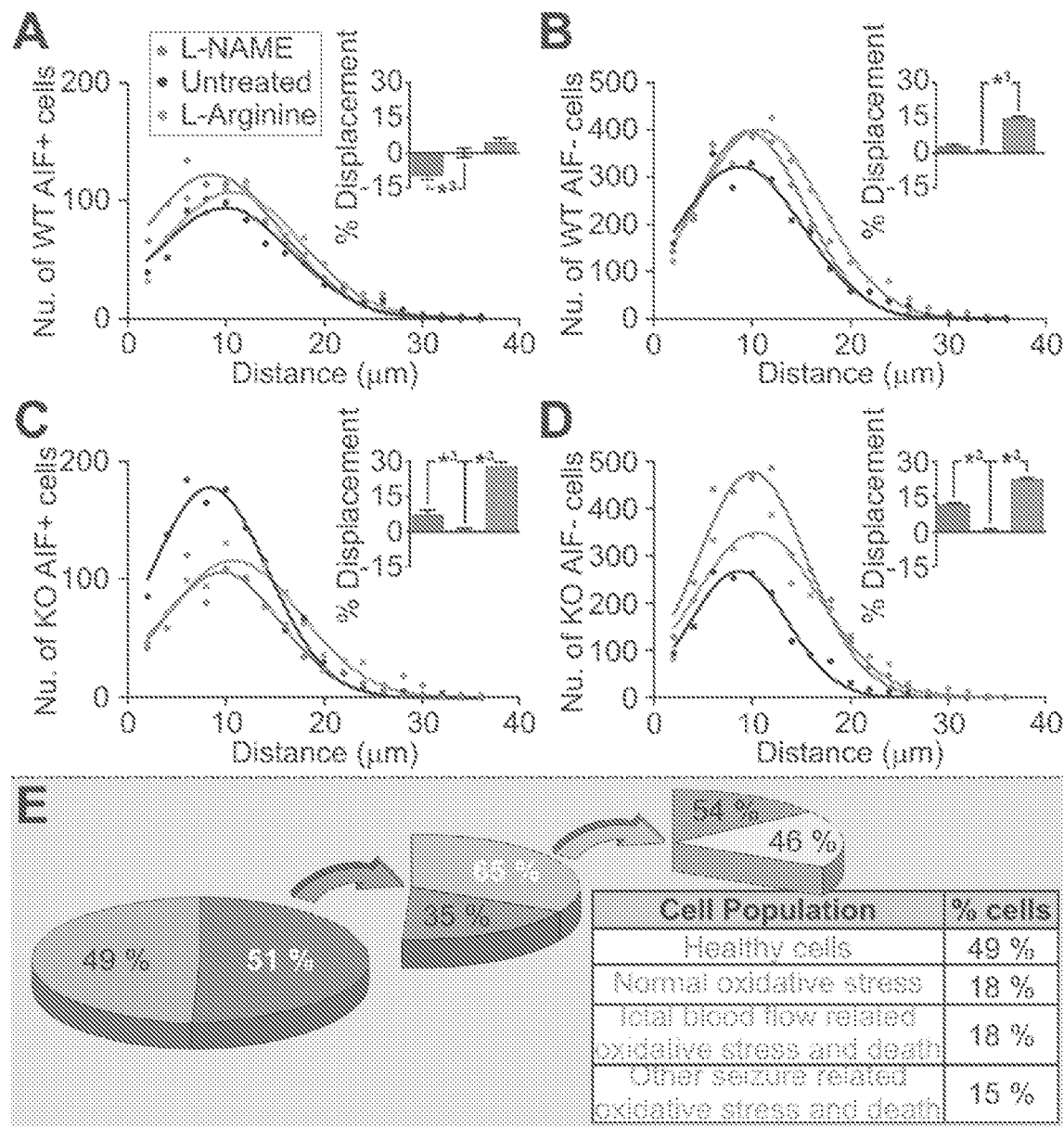
FIG. 10 is a graphical illustration of stereo logical analysis of AIF+/− cell spatial correlation to vessels (A-D) and the contribution of blood flow factors in ictal neurodegeneration (E), in accordance with the present disclosure.
Figure 11:
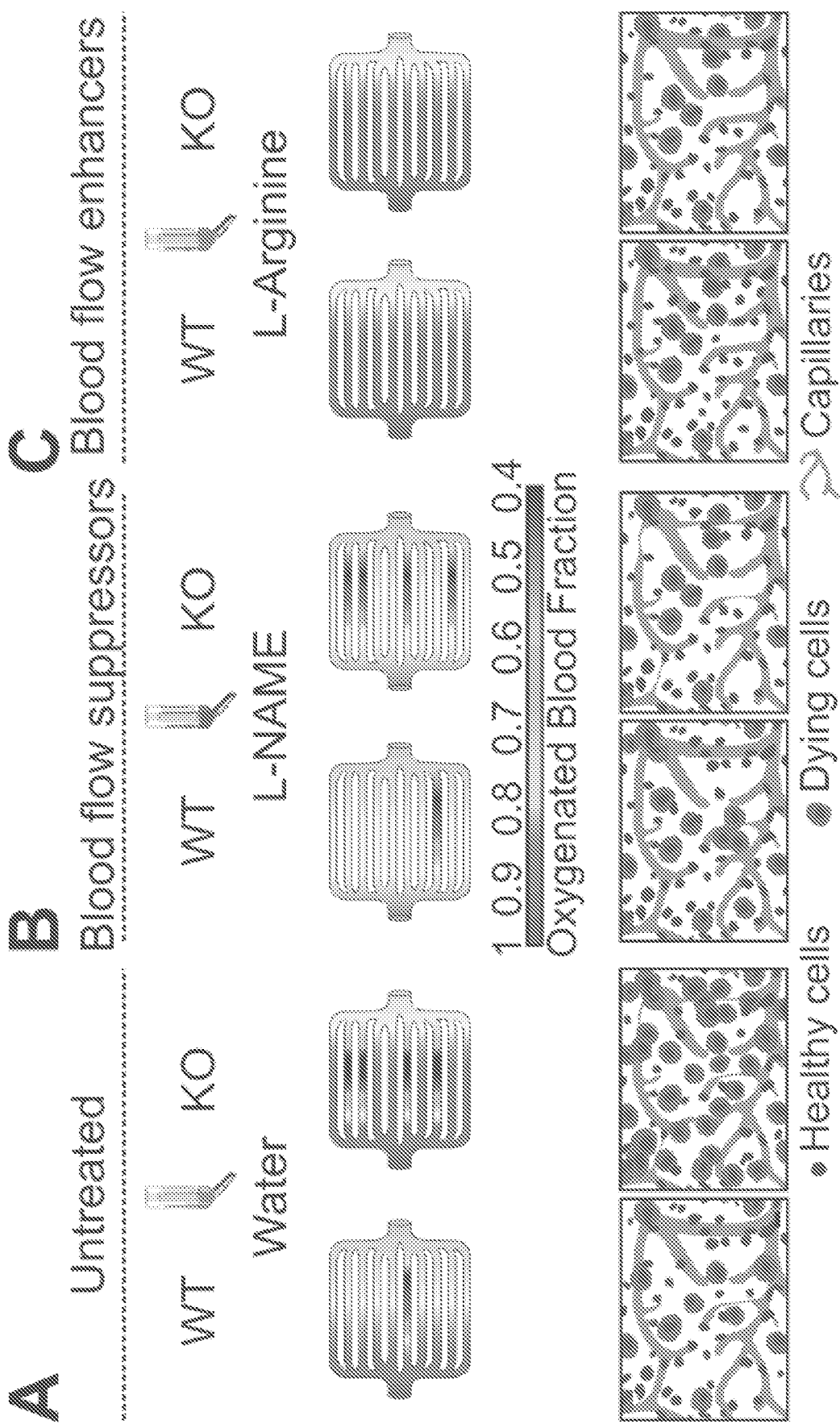
FIG. 11 is a graphical illustration of a model showing drug treatment effects (B,C) on cell death in epilepsy compared to untreated cells (A), in accordance with the present disclosure.

A contribution analysis of the drug treatment results suggests that abnormal blood flow accounts for as much as 54% of the neurodegeneration caused by epilepsy (FIG. 10E). The total normal hippocampal cell count was first determined in untreated WT animals, represented by the area of the leftmost pie chart in FIG. 10E. The percentage of healthy cells (49%) in untreated KO hippocampus was determined as the ratio of the number of KO AIF− cells to the total WT cell count. The remaining 51% of cells in untreated KOs either died or are dying, unhealthy, or oxidatively stressed (AIF+): the second pie chart's area is determined by the total amount of neurodegeneration. Not all oxidative stress may be due to epilepsy.

To determine the percentage of normal oxidative stress to be expected in healthy animals, the ratio of untreated WT AIF+ cells to the total number of degenerating cells found in untreated KO animals (35% of all unhealthy KO cells were determined to be from nonepilepsy sources that occur in healthy animals) was calculated. The remainder (65% of all neurodegeneration in untreated KO mice) represents the neurodegeneration due to epilepsy, as shown in FIG. 10E. The difference between the number of dead and dying cells in the sham versus L-Arginine treated KO animals reveals that as much as 54% of ictal neurodegeneration was due to abnormal blood flow in the untreated animal (18% of all hippocampal cells) whereas 46% of the neurodegeneration (15% of all hippocampal cells) arised from other sources of death and oxidative stress, such as excitotoxicity.

In summary, the damaging effects of epilepsy are insidious: seizure-driven neural degeneration accumulates over time, especially in the hippocampus, leading to sclerosis, cognitive decline, or death. Excitotoxicity driven by calcium overload is the prevalent model to explain ictal degeneration, though the same pro-apoptotic molecular cascades are activated during hypoxia, and therefore current molecular labeling technology cannot distinguish between neurodegeneration mediated by excitotoxicity versus hypoxia. Using a novel fluorescent labeling approach, in accordance with the present disclosure, a new model was tested regarding the possibility that abnormal pericyte-driven capillary constrictions/vasospasms-elicited by seizures-lead to hypoxic micro-ischemic events, non-uniform blood flow in capillary beds, and progressive hippocampal neurodegeneration.

Using the approach of the present disclosure, genetic rodent models that recapitulate human epilepsy (episodic ataxia type 1) were studied, with direct relevance to human temporal lobe epilepsy. Using methods and diagnostic kit, in accordance with the present disclosure, these studies demonstrated for the first time that normal and abnormal ictal hippocampal and cortical vasoconstrictions in vivo are driven by pericytes, by using awake and spontaneously epileptic animals and their wild-type (WT) littermates. To ensure that the results generalized to other forms of epilepsy, WT animals made epileptic in the classic kainic-acid (KA) experimental model of epilepsy were also employed. Experimental results, as detailed above, found that pericyte vasoconstrictions occur in abnormally high number and magnitude in the hippocampus of awake epileptic mice, and that neurodegeneration is tightly coupled spatially to pericyte driven strictures in the microvasculature, accounting for most neuronal death in epilepsy. Furthermore, it was shown that chronic oral administration of blood flow regulating drugs decreases ictal oxidative stress and neurodegeneration, suggesting that chronic blood flow enhancing treatments may be effective in reducing ictal neurodegeneration in human patients.

Because the Caspase molecular apoptotic pathway is activated by both hypoxia and excitotoxicity, there are no molecular labels to distinguish between hypoxia and excitotoxicity apoptotic mechanisms. Therefore a novel stereological method was developed to distinguish cell death driven by these two mechanisms by investigating the distance of oxidative stress from vessels, as described in detail below, should be random for excitotoxicity and non-random for hypoxia due to the primary role of the vasculature only in hypoxia. Analyses revealed that apoptotic neurons in epileptic animals are tightly-coupled in proximity to the hippocampal microvasculature, as compared to non-apoptotic cells, and that pericytes drive microvessel strictures in abnormally high number in epilepsy. This indicates that abnormal pericyte-driven vasospasmic ischemia-induced hypoxia in hippocampal capillary beds contributes to ictal neurodegeneration, because excitotoxicity has no known spatial association to the vasculature.

Figure 12:
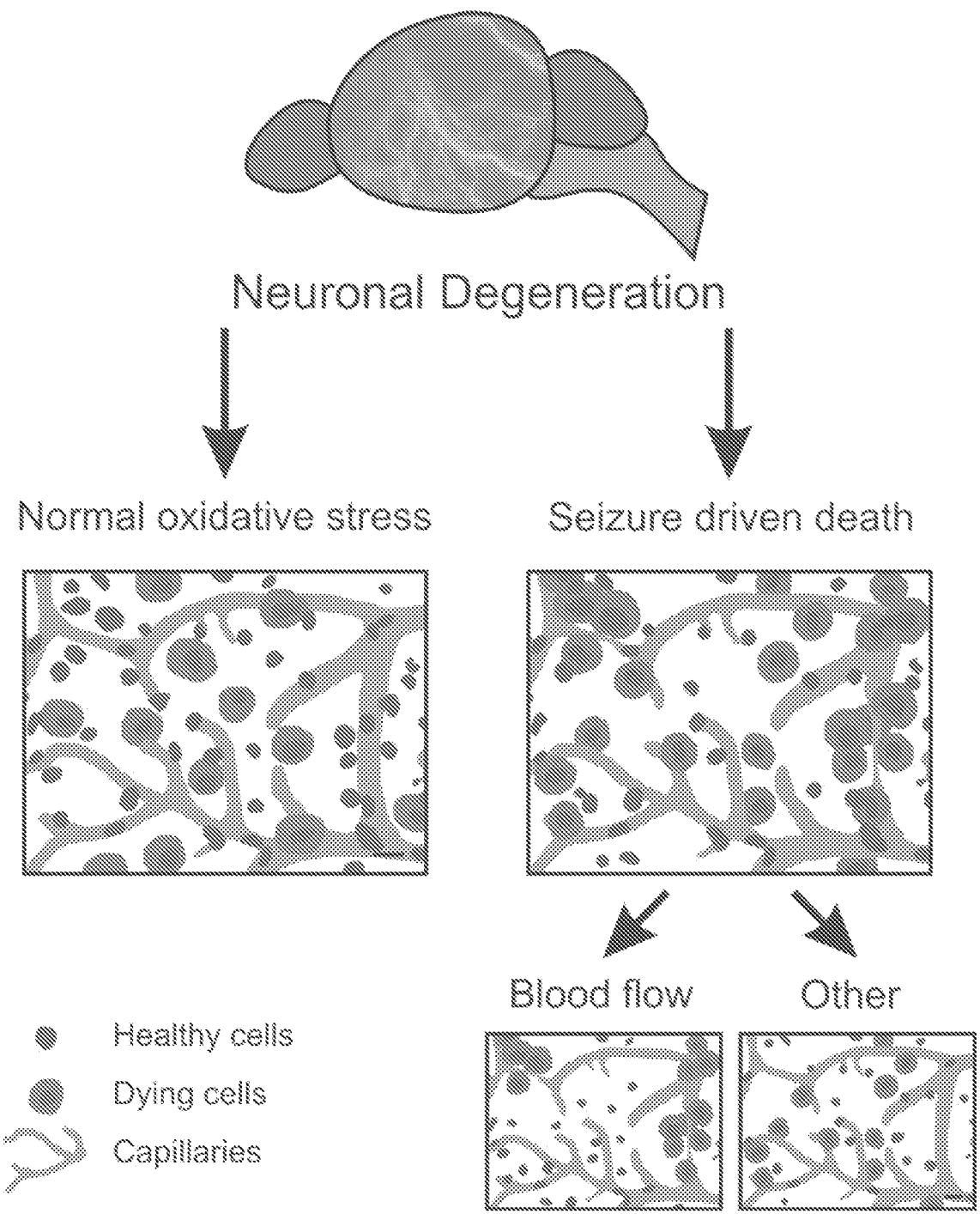
FIG. 12 is a schematic representing a model of neuronal degeneration in epilepsy, in accordance with the present disclosure.

Experimental results, as described in detail, provide a mechanism to reconcile these seemingly contradictory reports, where epileptic seizures drive cell death through both excitotoxicity and pericyte-driven vasospasmic ischemia. Specifically, as shown in the schematic of FIG. 12, neural degeneration can occur due to normal oxidative stress (non-epileptic sources of cell death), or through epilepsy. In particular, epilepsy can further cause a macroscopically hyperemic seizure focus that leads to both cell death from hypoxic apoptosis associated with abnormal vasospasms near ischemic vessels, or from other types of cell death (i.e. excitotoxicity) in which cell distances from vessels are spatially random. The combined result is that AIF+ cells tend to be nearer to blood vessels than (randomly distributed) AIF− cells. The results do not contradict findings that increased neuronal activity leads to excitotoxicity and hyperemia in the ictal focus. Rather, this model reconciles abnormal ictal blood flow with excitoxicity, positing that cells near ischemic capillaries become hypoxic, adding to the cell death brought about by excitoxicity-driven apoptosis (FIG. 5C).

The model of FIG. 12 can furthermore explain observations of a hyperemic focus with hyperoxic draining veins, despite the presence of simultaneous hypoxia. As such, local pockets of hypoxia occur due to the vasospasms found, leading to increased vascular irrigation in the focus. The hyperemic influx, however, is shunted through non-ischemic vessels (because the vasospasm keeps the oxygen from reaching the cells that need it), leading to increased metabolic rate in the focus. The surplus of oxygenated blood is then discarded via local draining veins, explaining the reports of macroscopic reddening of the draining veins, which were previously misinterpreted to mean that there was no ischemia in the ictal focus: evidence herein shows that there is indeed ischemia at the microscopic level. Capillaries, which are smaller in diameter than red blood cells, may become blocked when constructed even partially—stopping the flow of serum entirely—due to the pericyte constrictions, because the blood cells, especially leukocytes, which are themselves larger than the capillaries they flow within, clog the flow of serum at the point of constriction.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for identifying a subject condition, the method comprising:
    administering intravenously to a subject an effective amount of an injectable solution comprising fluorescent conjugated Dextran markers, having a molecular weight in a range between 3 kiloDaltons and 70 kiloDaltons, to selectively label pericytes throughout the subject's body;
    acquiring, using an imaging system, fluorescence signals originating from labeled pericytes to produce pericyte information associated with tissues of the subject's body; and
    generating a report identifying a subject condition using the pericyte information.

2. The method of claim 1, wherein the injectable solution comprises fluorescent markers diluted in an artificial cerebrospinal fluid with a concentration having values between 16 mg/Kg and 25 mg/Kg.

3. The method of claim 1, wherein the imaging system includes a confocal imaging system or a two-photon microscopy system configured to acquire the fluorescence signals from intravenously labeled pericytes.

4. The method of claim 1, wherein generating the report further includes determining a likelihood of vasospasmic activity using the pericyte information.

5. The method of claim 1, wherein the tissues of the subject's body include blood vessels.

6. The method of claim 1, wherein the subject condition includes a blood flow constriction.

7. The method of claim 1, wherein the subject condition includes a neural degeneration.

8. A method for treating a subject condition, the method comprising:
   administering intravenously to a subject an effective amount of an injectable solution comprising fluorescent conjugated Dextran markers, having a molecular weight in a range between 3 kiloDaltons and 70 kiloDaltons, to selectively label pericytes throughout the subject's body;
   acquiring, using an imaging system, fluorescence signals originating from labeled pericytes to produce pericyte information associated with tissues of the subject's body;
   identifying a subject condition using the pericyte information; and
   adapting a treatment using the identified subject condition.

9. The method of claim 8, wherein the injectable solution comprises fluorescent markers diluted in an artificial cerebrospinal fluid with a concentration having values between 16 mg/Kg and 25 mg/Kg.

10. The method of claim 8, wherein the imaging system includes a confocal imaging system or a two-photon microscopy system to acquire the fluorescence signals from intravenously labeled pericytes.

11. The method of claim 8, wherein the tissues of the subject's body include blood vessels.

12. The method of claim 8, wherein the treatment includes administration of at least one drug.

13. A method for staining pericytes in a subject, the method comprising steps of:
   providing an effective amount of an injectable solution comprising fluorescently conjugated dextran, the fluorescently conjugated dextran having a molecular weight in a range between 3 kiloDaltons and 70 kiloDaltons and being capable of selectively labeling pericytes throughout the subject; and
   administering intravenously to the subject the effective amount of the injectable solution such that the fluorescently conjugated dextran selectively binds to pericytes in the subject.

14. The method of claim 13 and further comprising acquiring, using an imaging system, signals from the fluorescently conjugated dextran that has selectively bound to the pericytes.

15. The method of claim 13 wherein the fluorescently conjugated dextran has a molecular weight of about 10 kiloDaltons.

16. The method of claim 13 and further comprising co-staining the pericytes with a second pericyte-specific marker.

* * * * *